United States Patent
Schramm et al.

(10) Patent No.: US 11,114,184 B2
(45) Date of Patent: Sep. 7, 2021

(54) DNA METHYLTRANSFERASE 1 TRANSITION STATE STRUCTURE AND USES THEREOF

(71) Applicant: Albert Einstein College of Medicine, Bronx, NY (US)

(72) Inventors: Vern L. Schramm, New Rochelle, NY (US); Quan Du, Bronx, NY (US); Zhen Wang, Feicheng (CN)

(73) Assignee: ALBERT EINSTEIN COLLEGE OF MEDICINE, Bronx, NY (US)

( * ) Notice: Subject to any disclaimer, the term of this patent is extended or adjusted under 35 U.S.C. 154(b) by 638 days.

(21) Appl. No.: 15/895,057

(22) Filed: Feb. 13, 2018

(65) Prior Publication Data

US 2018/0239878 A1 Aug. 23, 2018

Related U.S. Application Data

(60) Provisional application No. 62/461,268, filed on Feb. 21, 2017.

(51) Int. Cl.
*G16C 20/50* (2019.01)
*C12Q 1/48* (2006.01)
*C12N 9/10* (2006.01)
*G16C 20/10* (2019.01)
*G16B 15/00* (2019.01)

(52) U.S. Cl.
CPC .......... *G16C 20/50* (2019.02); *C12N 9/1007* (2013.01); *C12Q 1/48* (2013.01); *C12Y 201/01037* (2013.01); *G16B 15/00* (2019.02); *G16C 20/10* (2019.02)

(58) Field of Classification Search
None
See application file for complete search history.

(56) References Cited

U.S. PATENT DOCUMENTS

| | | |
|---|---|---|
| 6,121,296 A | 9/2000 | Schramm et al. |
| 6,693,193 B1 | 2/2004 | Furneaux et al. |
| 7,022,852 B2 | 4/2006 | Furneaux et al. |
| 7,211,677 B2 | 5/2007 | Furneaux et al. |
| 7,405,297 B2 | 7/2008 | Furneaux et al. |
| 7,777,025 B2 | 8/2010 | Schramm et al. |
| 8,541,567 B2 | 9/2013 | Schramm |
| 2007/0037223 A1* | 2/2007 | Kaneko ................ G01N 33/60 435/7.5 |
| 2007/0275988 A1 | 11/2007 | Schramm |
| 2010/0062995 A1 | 3/2010 | Schramm |
| 2011/0301104 A1 | 12/2011 | Schramm |

OTHER PUBLICATIONS

Ye et al. Analytical Biochemistry 401, 2010, 168-172.*
Scott et al. Methods in Enzymology, 317, 2000, pp. 18-38 (see Abstract).*
Du Q et al., entitled "Human DNMT1 transition state structure," PNAS, Mar. 15, 2016, vol. 113, No. 11, pp. 2916-2921,www.pnas.org/cgi/doi/10.1073/pnas.1522491113; Supporting Information 1 page; SI Appendix 19 pages; Epub Feb. 29, 2016.

* cited by examiner

*Primary Examiner* — Michael L Borin
(74) *Attorney, Agent, or Firm* — Fox Rothschild, LLP

(57) ABSTRACT

Methods and systems for obtaining inhibitors of human DNA methyltransferase 1 (DNMT1) are disclosed where the methods involve designing compounds that resemble the DNMT1 transition state.

5 Claims, 5 Drawing Sheets
Specification includes a Sequence Listing.

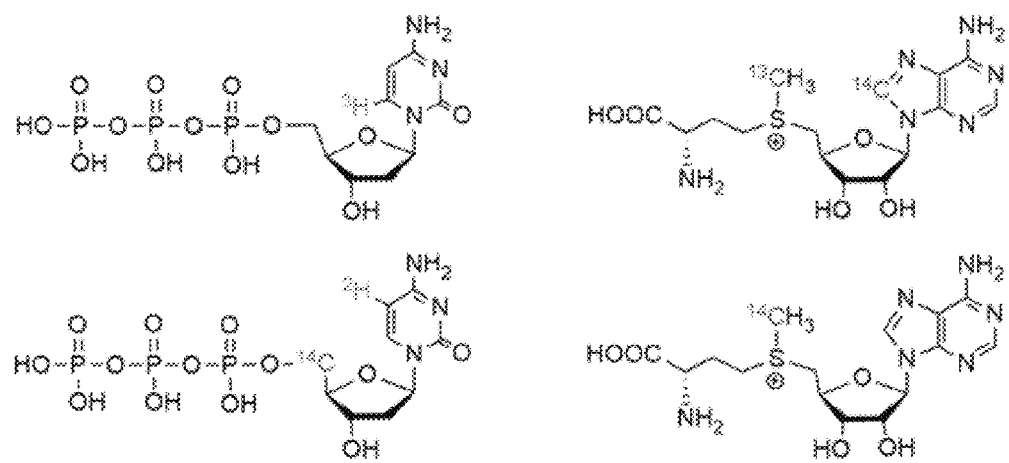
FIG. 2A
```
5'-CTACCTTGGTAT
   GATGGAACCATAGCTAACCATACTCA-5'
                m
         DNA polymerase | dATP, dCTP, dGTP, dTTP
                        ↓
5'-CTACCTTGGTATCGATTGGTATGAGT
   GATGGAACCATAGCTAACCATACTCA-5'
                m
```
FIG. 2B
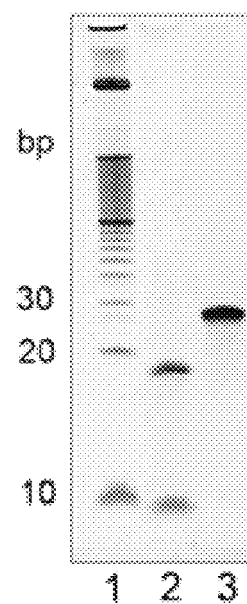
FIG. 2C

US 11,114,184 B2

DNA METHYLTRANSFERASE 1 TRANSITION STATE STRUCTURE AND USES THEREOF

CROSS-REFERENCE TO RELATED APPLICATION

This application claims the benefit of U.S. Provisional Patent Application No. 62/461,268 filed Feb. 21, 2017, the contents of which are herein incorporated by reference in their entirety.

STATEMENT OF GOVERNMENT SUPPORT

This invention was made with government support under grant numbers GM041916 and CA135405 awarded by the National Institutes of Health. The government has certain rights in the invention.

BACKGROUND OF THE INVENTION

Throughout this application various publications are referred to in parentheses. Full citations for these references may be found at the end of the specification before the claims. The disclosures of these publications are hereby incorporated by reference in their entireties into the subject application to more fully describe the art to which the subject application pertains.

Deoxyribonucleic acid (DNA) methyltransferase (DNMT) catalyzes methyl transfer reactions on DNA cytosine residues. DNMT is a validated anticancer target. Two drugs have been approved by U.S. Food and Drug Administration; however, those DNMT inhibitors (5-aza-cytidine, 5-aza-deoxycytidine) are mutagenic, are incorporated into DNA and cause genomic mutations. The present invention uses the human DNMT1 transition state (TS) to address the need for new inhibitors for human DNMT1, which will be effective in cancer therapy.

SUMMARY OF THE INVENTION

Systems and methods are disclosed for obtaining inhibitors of human DNA methyltransferase 1 (DNMT1) by designing and/or obtaining compounds that resemble the charge and geometry of the DNMT1 transition state (TS).

BRIEF DESCRIPTION OF THE DRAWINGS

FIG. 2A-2D. Development of chemical tools for ME measurement on DNMT1. (A) Examples of reactant radiolabels: [6-$^3$H]- and [5-$^2$H, 5'-$^{14}$C]-dCTPs and [Me-$^{14}$C]- and [Me-$^{13}$C, 8-$^{14}$C]-SAMs. Remote labels (5'-$^{14}$C for DNA, 8-$^{14}$C for SAM) were used as radioactive reporters for stable isotopes (e.g., $^2$H, $^{13}$C). (B) Incorporation of specifically labeled dCTPs into a 26-bp hemimethylated DNA by Klenow (exo-) extension. Note the premethylated CpG dinucleotide in the template strand. From top to bottom: SEQ ID NO:2, 3, 4 and 3. (C) Analysis of DNA synthesis by nondenaturing polyacrylamide gel and fluorescent staining. Lanes 1-3: 10-bp DNA ladder, DNA template and primer (upper and lower bands), and 26-bp DNA product. (D) Radiometric quantitation of hemimethylated DNA and its fully methylated product was analyzed by the dC and 5m-dC nucleosides in hydrolyzed DNA.

DETAILED DESCRIPTION OF THE INVENTION

Figure 1A:
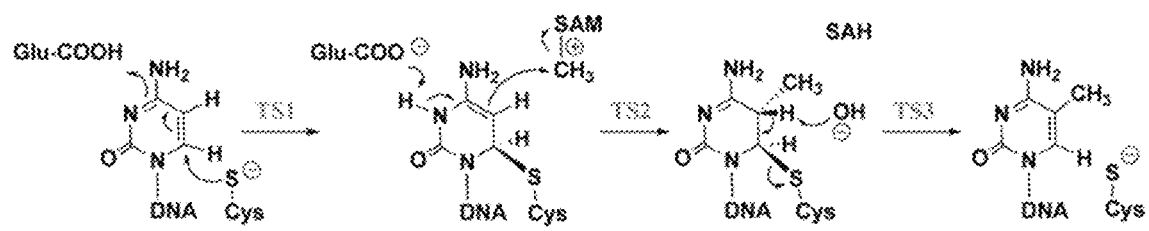
FIG. 1A-1B. DNA methylation catalyzed by DNMT1. (A) Proposed catalytic mechanism for DNMT1 involves three chemical TSs (TS1, TS2, and TS3). Cys, Cysteine; Glu, Glutamic acid; SAH, S-adenosylhomocysteine; SAM, S-adenosyl-l-methionine. Cys attack at TS1 brings a negative charge (−1) to the Cyt ring, whereas Cys withdrawal after TS3 restores the aromaticity of the Cyt. (B) Based on the KIE analysis presented here, methyl transfer is chemically rate-limiting for DNMT1 and has a higher energy barrier than the thiol-attack and β-elimination steps. Small forward commitments demonstrate the chemical steps to have a higher energy barrier than the binding and release of substrates.

The invention provides a computer-implemented, experimentally-guided kinetic isotope effect method of obtaining an inhibitor of human DNA methyltransferase 1 (DNMT1), the method comprising using a computer to design a chemically stable compound that resembles the charge and geometry of the DNMT1 transition state, wherein the compound is a putative inhibitor of DNMT1.

The invention also provides a system for obtaining a putative inhibitor of a human DNA methyltransferase 1 (DNMT1) comprising one or more data processing apparatus and a computer-readable medium coupled to the one or more data processing apparatus having instructions stored thereon that when executed by the one or more data processing apparatus cause the one or more data processing apparatus to perform a method comprising designing a chemically stable compound that resembles the charge and geometry of the DNMT1 transition state, wherein the compound is a putative inhibitor of DNMT1.

The invention further provides a computer-implemented method for detecting or screening for a compound that is an inhibitor of human DNA methyltransferase 1 (DNMT1), the method comprising the steps of:

(i) inputting into the computer values for the molecular electrostatic potential at the van der Waals surface computed from the wave function of a DNMT1 transition state and values for the geometric atomic volume of the DNMT1 transition state, wherein the DNMT1 transition state comprises the structure

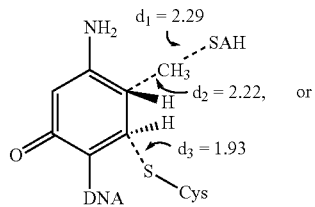

or (ii) using chemical logic aided by computer design to obtain a chemically stable compound that resembles the molecular electrostatic potential at the van der Waals surface computed from the wave function of the DNMT1 transition state and the geometric atomic volume of the DNMT1 transition state;
(iii) optionally synthesizing the compound; and
(iv) optionally testing the compound for inhibitory activity to DNMT1;
to thereby detect or screen for a compound that is an inhibitor of DNMT1.

The invention further provides a method of detecting, screening for or designing an inhibitor of human DNA methyltransferase 1 (DNMT1), the method comprising the steps of:
(i) measuring kinetic isotope effects on the DNMT1-catalyzed methylation of hemimethylated DNA to obtain the DNMT1 transition state structure,
wherein the DNMT1 transition state comprises the structure

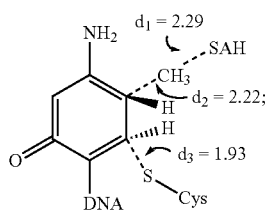

(ii) determining the molecular electrostatic potential at the van der Waals surface computed from the wave function of the DNMT1 transition state and the geometric atomic volume of the DNMT1 transition state;
(iii) obtaining a chemically stable compound that resembles the molecular electrostatic potential at the van der Waals surface computed from the wave function of the DNMT1 transition state and the geometric atomic volume of the DNMT1 transition state; and
(iv) testing the compound for inhibitory activity to DNMT1 by determining if the compound inhibits DNMT1-catalyzed methylation of hemimethylated DNA;
wherein a compound that inhibits DNMT1-catalyzed methylation of hemimethylated DNA is an inhibitor of DNMT1;
thereby detecting, screening for or designing an inhibitor of human DNA methyltransferase 1 (DNMT1).

The invention also provides a system comprising a non-transitory computer-readable medium coupled to one or more data processing apparatus having instructions stored thereon which, when executed by the one or more data processing apparatus, cause the one or more data processing apparatus to perform a method comprising:
(i) using experimental kinetic isotope effects and quantum chemical analysis on human DNA methyltransferase 1 (DNMT1)-catalyzed methylation of hemimethylated DNA to obtain the DNMT1 transition state structure,
wherein the DNMT1 transition state comprises the structure

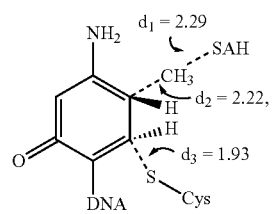

(ii) calculating a molecular electrostatic potential at the van der Waals surface computed from the wave function of the DNMT1 transition state and the geometric atomic volume of the DNMT1 transition state; and
(iii) identifying in silico from a library of compounds a chemically stable compound that resembles the molecular electrostatic potential at the van der Waals surface computed from the wave function of the DNMT1 transition state and the geometric atomic volume of the DNMT1 transition state;
wherein the chemically stable compound that resembles the molecular electrostatic potential at the van der Waals surface computed from the wave function of the DNMT1 transition state and the geometric atomic volume of the DNMT1 transition state is a putative inhibitor of DNMT1.

The invention also provides a system comprising a non-transitory computer-readable medium coupled to one or more data processing apparatus having instructions stored thereon which, when executed by the one or more data processing apparatus, cause the one or more data processing apparatus to perform a method comprising:
(i) determining the molecular electrostatic potential at the van der Waals surface computed from the wave function of a human DNA methyltransferase 1 (DNMT1) transition state and the geometric atomic volume of the DNMT1 transition state, wherein the DNMT1 transition state comprises the structure

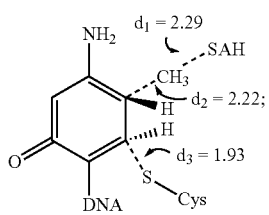

and
(ii) designing a chemically stable compound that resembles the molecular electrostatic potential at the van der Waals surface computed from the wave function of the DNMT1 transition state and the geometric atomic volume of the DNMT1 transition state;

wherein a chemically stable compound that resembles the molecular electrostatic potential at the van der Waals surface computed from the wave function of the DNMT1 transition state and the geometric atomic volume of the DNMT1 transition state is a putative inhibitor of DNMT1.

The invention also provides a computer-implemented method performed using a system comprising a non-transitory computer-readable medium coupled to one or more data processing apparatus having instructions stored thereon, the methods comprising:

(i) using kinetic isotope effects on human DNA methyltransferase 1 (DNMT1)-catalyzed methylation of hemimethylated DNA to obtain the DNMT1 transition state structure, wherein the DNMT1 transition state comprises the structure

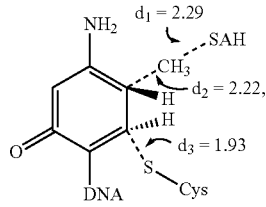

(ii) determining the molecular electrostatic potential at the van der Waals surface computed from the wave function of the DNMT1 transition state and the geometric atomic volume of the DNMT1 transition state; and (iii) identifying from a library of compounds a chemically stable compound that resembles the molecular electrostatic potential at the van der Waals surface computed from the wave function of the DNMT1 transition state and the geometric atomic volume of the DNMT1 transition state;

wherein the chemically stable compound that resembles the molecular electrostatic potential at the van der Waals surface computed from the wave function of the DNMT1 transition state and the geometric atomic volume of the DNMT1 transition state is a putative inhibitor of DNMT1.

The invention also provides a computer implemented method performed using a system comprising a non-transitory computer-readable medium coupled to one or more data processing apparatus having instructions stored thereon, the methods comprising:

(i) determining the molecular electrostatic potential at the van der Waals surface computed from the wave function of a human DNA methyltransferase 1 (DNMT1) transition state and the geometric atomic volume of the DNMT1 transition state, wherein the DNMT1 transition state comprises the structure

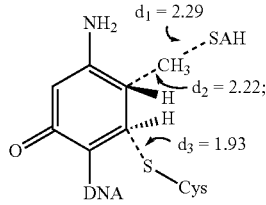

and (ii) designing a chemically stable compound that resembles the molecular electrostatic potential at the van der Waals surface computed from the wave function of the NSD2 transition state and the geometric atomic volume of the DNMT1 transition state;

wherein a chemically stable compound that resembles the molecular electrostatic potential at the van der Waals surface computed from the wave function of the DNMT1 transition state and the geometric atomic volume of the DNMT1 transition state is a putative inhibitor of DNMT1.

The methods can also comprise synthesizing the putative inhibitor compound and/or testing the compound for inhibitory activity to DNMT1.

The invention also provides a method of manufacturing an inhibitor of human DNA methyltransferase 1 (DNMT1); the method comprising:

(i) obtaining information regarding the design of a chemically stable compound that resembles the molecular electrostatic potential at the van der Waals surface computed from the wave function of the DNMT1 transition state and the geometric atomic volume of the DNMT1 transition state according to any of the methods or systems disclosed herein;

(ii) synthesizing the compound; and (iii) optionally testing the compound for inhibitory activity to DNMT1; to thereby manufacture a compound that is an inhibitor of DNMT1.

The invention also provides methods of inhibiting DNMT1 comprising obtaining a DNMT1 inhibitor compound by any of the methods disclosed herein or by using any of the systems disclosed herein, and contacting DNMT1 with the compound.

The invention further provides methods of treating a subject having a cancer comprising obtaining a DNMT1 inhibitor by any of the methods disclosed herein or by using any of the systems disclosed herein, and administering the compound to the subject in an amount effective to inhibit DNMT1. The subjects can have different types of cancers, including but not limited to, a multiple myeloma, a neuroblastoma, a glioblastoma, prostate cancer and/or breast cancer.

The invention still further provides compounds obtained by any of the methods disclosed herein or by using any of the systems disclosed herein.

As used herein, a compound resembles the DNMT1 transition state molecular electrostatic potential at the van der Waals surface computed from the wave function of the transition state and the geometric atomic volume if that compound has an $S_e$ and $S_g \geq 0.5$, where $S_e$ and $S_g$ are determined as in Formulas (1) and (2) on page 8831 of Bagdassarian, Schramm and Schwartz, 1996 (38).

Page 8831 of Bagdassarian et al. 1996 (58) sets forth in part "[a] molecule can be compared to another either geometrically or electrostatically, but ideally, a similarity measure will contain a mixture of both. Consider first the measure $$S_e = \frac{\sum_{i=1}^{nA}\sum_{j=1}^{nB} \epsilon_i^A \epsilon_j^B \exp(-\alpha r_{ij}^2)}{\sqrt{\sum_{i=1}^{nA}\sum_{j=1}^{nA} \epsilon_i^A \epsilon_j^A \exp(-\alpha r_{ij}^2)} \sqrt{\sum_{i=1}^{nB}\sum_{j=1}^{nB} \epsilon_i^B \epsilon_j^B \exp(-\alpha r_{ij}^2)}} \quad (1)$$

where $\epsilon_i^A$ is the electrostatic potential at surface point i of molecule A, $\epsilon_j^B$ defines point j of molecule B, and in the numerator $r_{ij}^2$ is the spatial distance squared between point i on A and j on B. nA and nB refer to the number of surface points on each molecule. The double summation is therefore over all possible interactions between points on the two molecules, and α is the length scale for the interaction between i and j. The numerator compares A to B for a particular orientation of molecule B relative to molecule A. The denominator serves as a normalization factor for the comparison of A to itself and for B to itself. Here, $r_{ij}^2$ refers to the distance between i and j on the same molecule. The distance between points is squared to decrease computation time. Consider also a second, purely geometrical measure:

$$S_g = \frac{\sum_{i=1}^{nA}\sum_{j=1}^{nB}\exp(-\alpha r_{ij}^2)}{\sqrt{\sum_{i=1}^{nA}\sum_{j=1}^{nA}\exp(-\alpha r_{ij}^2)}\sqrt{\sum_{i=1}^{nB}\sum_{j=1}^{nB}\exp(-\alpha r_{ij}^2)}}. \quad (2)$$

The invention provides methods and systems that provide a technical solution to enable obtaining inhibitors for DNMT1, particularly ones that will be effective in cancer therapy. The disclosed methods enhance the performance of the system in obtaining the inhibitors.

This invention will be better understood from the Experimental Details that follow. However, one skilled in the art will readily appreciate that the specific methods and results discussed are merely illustrative of the invention as described more fully in the claims that follow thereafter.

Experimental Details

EXAMPLE 1

Overview

Example 1 was previously published by the inventors as "Human DNMT1 transition state structure" in the Proceedings of the National Academy of Sciences, Vol. 113, No. 11, pages 2916-2921, 2016, Epub 2016 Feb. 29.

Summary

DNA methyltransferase 1 (DNMT1) is the major enzyme responsible for maintenance of DNA CpG methylation marks in human cells. Human DNMT1 maintains the epigenetic state of DNA by replicating CpG methylation signatures from parent to daughter strands, producing heritable methylation patterns through cell divisions. The enzyme is a validated target for cancer, but current treatments are mutagenic. Knowledge of the transition state (TS) structure of DNMT1 will inform the chemical reaction mechanism and provide information for TS analog design. The proposed catalytic mechanism of DNMT1 involves nucleophilic attack of Cys1226 to cytosine (Cyt) C6, methyl transfer from S-adenosyl-1-methionine (SAM) to Cyt C5, and proton abstraction from C5 to form methylated CpG in DNA. The subangstrom geometric and electrostatic character of the TS for the DNMT1 methylation of hemimethylated DNA are described. The experimental and computational TS analysis indicates methyl transfer is the rate-limiting chemical step for the reaction. Experimental kinetic isotope effects were used to guide quantum mechanical calculations to solve the TS structure. Methyl transfer occurs after Cys1226 attack to Cyt C6, and the methyl transfer step is chemically rate-limiting for DNMT1. Electrostatic potential maps were compared for the TS and ground states, providing the electronic basis for interactions between the protein and reactants at the TS. Methyl group transfer can be characterized as a loose nucleophilic substitution TS. TS analysis of DNMT1 demonstrates an approach to understand a complex epigenetic enzyme.

Introduction

Human DNA methyltransferases (DNMTs) catalyze the formation of 5-methylcytosine (5 mC) at CpG sites on DNA, a key epigenetic mark present in the human genome (1). DNA methylation is involved in transcriptional silencing, cellular differentiation, genomic imprinting, and X-chromosome inactivation. In addition, hypermethylation of CpG islands at gene promoter regions has been associated with carcinogenesis (2). Maintenance of DNA methylation patterns is conducted by human DNMT1, a multidomain protein of 1,616 amino acids. The C-terminal methyltransferase domain shows sequence similarities to the bacterial methyltransferases (3). Crystal structures of mouse and human DNMT1 complexed with different substrates have provided a structural basis for DNMT1-mediated maintenance DNA methylation (4, 5). Domain interactions and large conformational changes are responsible for properly positioning hemimethylated DNA within the active site and catalyze methyl transfer from S-adenosyl-1-methionine (SAM) to DNA. Site-directed mutations have offered insights into the structure-function relationship of DNMTs (6, 7), but their transition state (TS) structures have remained unknown.

DNMT1 has been proposed to follow a catalytic mechanism shared by bacterial DNA-(cytosine C5)-methyltransferases (4, 8-10): nucleophilic attack of cytosine (Cyt) C6 by Cys1226 of DNMT1, methyl transfer from SAM to Cyt C5, and β-elimination of H5 to produce 5 mC in the final step (FIG. 1). Recent quantum mechanics (QM)/molecular mechanics (MM) and molecular dynamics (MD) simulations of the bacterial M.HhaI methyltransferase suggested that Cys1226 attack is concerted with methyl transfer (11, 12), and that β-elimination of H5 is the rate-limiting step (12). The combination of kinetic isotope effects (KIEs) and computational chemistry can test predicted reaction mechanisms and can provide a model of the TS structure.

Enzymes catalyze reactions by forming short-lived TSs from their reactants held in Michaelis complexes (13). The lifetime of a chemical TS is typically around $10^{-14}$ s, on the time scale of chemical bond vibrations. No spectroscopic method is generally available to observe the chemical structure of TSs directly for enzymatic reactions (14). TS analysis based on experimental KIEs has provided detailed chemical insights into the catalytic mechanisms of enzymes acting mostly on small molecules and has led to the design of some of the most powerful enzyme inhibitors (15, 16). Enzymes in epigenetic regulations often involve large and complex substrates, creating experimental challenges in both ME measurements and computational models. Nonetheless, TS analysis can be applied to complex enzyme systems, including the 50S ribosomes (17), as long as the chemical steps can be interrogated with the appropriate isotope labels.

In the present study, 10 experimental KIEs were measured to investigate the TS and catalytic mechanisms of human DNMT1. By combining these experimental KIE values with QM calculations, the subangstrom TS structure was established for human DNMT1. The results also show methyl transfer to be the major chemical barrier in the reaction coordinate, rather than the Cys attack, β-elimination from the C5-position, or departure of the 5-methyl Cyt from the catalytic site Cys. The work demonstrates an experimental approach to analyze the TS structures of complex epigenetic enzymes, for unraveling their catalytic mechanisms, and for advancing target-specific drug designs.

Materials and Methods

Human DNMT1 has the following amino acid sequence (NCBI Reference Sequence: NP_001370.1, SEQ ID NO:1):

```
   1 mpartaparv ptlavpaisl pddvrrrlkd lerdslteke
     cvkeklnllh eflqteiknq 61 lcdletklrk eelseegyla kvksllnkdl slengahayn
     revngrleng nqarsearrv 121 gmadansppk plskprtprr sksdgeakpe pspspritrk
     strqttitsh fakgpakrkp 181 qeeseraksd esikeedkdq dekrrrvtsr ervarplpae
     eperaksgtr tekeeerdek 241 eekrirsqtk eptpkqklke epdrearagv qadededgde
     kdekkhrsqp kdlaakrrpe 301 ekepekvnpq isdekdedek eekrrkttpk eptekkmara
     ktvmnskthp pkciqcgqyl 361 ddpdlkygqh ppdavdepqm ltneklsifd anesgfesye
     alpqhkltcf svyckhghlc 421 pidtgliekn ielffsgsak piydddpsle ggvngknlgp
     inewwitgfd ggekaligfs 481 tsfaeyilmd pspeyapifg lmqekiyisk ivveflqsns
     dstyedlink iettvppsgl 541 nlnrftedsl lrhaqfvveq vesydeagds deqpifltpc
     mrdliklagv tlgqrraqar 601 rqtirhstre kdrgptkatt tklvyqifdt ffaeqiekdd
     redkenafkr rrcgvcevcq 661 qpecgkckac kdmvkfggsg rskqacqerr cpnmamkead
     ddeevddnip empspkkmhq 721 gkkkkqnknr iswvgeavkt dgkksyykkv cidaetlevg
     dcvsvipdds skplylarvt 781 alwedssngq mfhahwfcag tdtvlgatsd plelflvdec
     edmqlsyihs kvkviykaps 841 enwameggmd pesllegddg ktyfyqlwyd qdyarfespp
     ktqptednkf kfcvscarla 901 emrqkeiprv leqledldsr vlyysatkng ilyrvgdgvy
     lppeaftfni klsspvkrpr 961 kepvdedlyp ehyrkysdyi kgsnldapep yrigrikeif
     cpkksngrpn etdikirvnk 1021 fyrpenthks tpasyhadin llywsdeeav vdfkavqgrc
     tveygedlpe cvqvysmggp 1081 nrfyfleayn aksksfedpp nharspgnkg kgkgkgkgkp
     ksqacepsep eieiklpklr 1141 tldvfsgcgg lsegfhqagi sdtlwaiemw dpaaqafrln
     npgstvfted cnillklvma 1201 gettnsrgqr lpqkgdveml cggppcqgfs gmnrfnsrty
     skfknslvvs flsycdyyrp 1261 rffllenvrn fvsfkrsmvl kltlrclvrm gyqctfgvlq
     agqygvaqtr rraiilaaap 1321 geklplfpep lhvfapracq lsvvvddkkf vsnitrlssg
     pfrtitvrdt msdlpevrng 1381 asaleisyng epqswfqrql rgaqyqpilr dhickdmsal
     vaarmrhipl apgsdwrdlp 1441 nievrlsdgt marklrythh drkngrsssg alrgvcscve
     agkacdpaar qfntlipwcl 1501 phtgnrhnhw aglygrlewd gffsttvtnp epmgkqgrvl
     hpeqhrvvsv recarsqgfp 1561 dtyrlfgnil dkhrqvgnav ppplakaigl eiklcmlaka
     resasakike eeaakd.
```

Human DNMT1. Full-length human DNMT1 protein (amino acids 1-1,616) containing an N-terminal His6-tag was expressed in a Sf9 insect cell line as described previously (33). The expressed human DNMT1 was purified by nickel-nitrilotriacetic acid column chromatography on FPLC. The concentrated DNMT1 was further purified through a gel filtration column (200 pg, Hiload 16/600 Superdex; Amersham) in 50 mM Hepes (pH 7.4), 150 mM NaCl, and 1mMDTT to remove low-molecular-weight contaminants. Purified DNMT1 appeared as a single band on SDS/PAGE with an apparent size of 190 kDa. Aliquots were frozen and stored at −80° C.

Forward Commitment Values. The Cf values were measured by substrate trapping procedures. The formation of radiolabeled product was quantitated after chasing enzyme-bound labeled substrate with a large excess of unlabeled substrate. The procedures involved HPLC separation and liquid scintillation counting (LSC) of the [5'-$^3$H]-labeled 5 m-dC or the [1'-$^3$H]-labeled S-adenosylhomocysteine product in respective experiments.

Figure 2D:
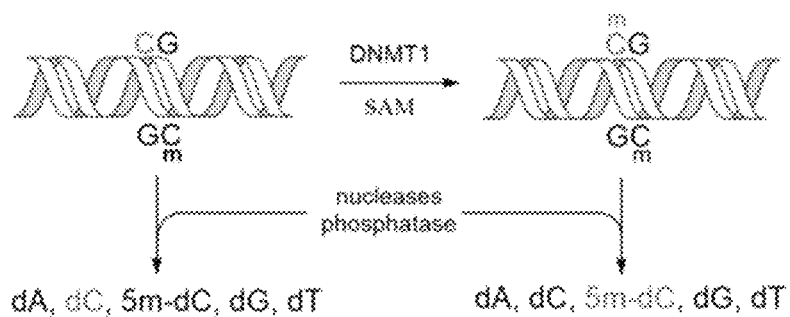

Measurement of DNA Cyd KIEs. KIEs were measured by internal competition using a mixture of isotope-labeled (heavy) and remote-labeled (light) DNA substrates. $^{14}$C— and $^3$H—labeled hemimethylated 26-bp DNA and 1.0 mM nonlabeled SAM were incubated in a buffer of 20 mMTris.HCl (pH 7.4), 100 mM KCl, and 1 mM DTT at 37° C. The methylation reaction was initiated by the addition of human DNMT1. Reactions were quenched at different reaction intervals by placing tubes in a 95° C. heat block for 10 min, followed by cooling on ice. The quenched reactions (100 μL) were treated with 20 μL of 10 mM Tris.HCl (pH 7.9), 50 mM NaCl, 10 mM MgCl$_2$, 1 mM DTT, 10 units of exonuclease III, 0.1 unit of snake venom phosphodiesterase I, and 0.5 unit of alkaline phosphatase. The DNA digestion (37° C. overnight) converted all DNA to mononucleosides (FIG. 2D).

The nucleoside mixture from each reaction aliquot was separated by a C18 column on an HPLC system equipped with a photodiode array detector. Cold carriers of dC and 5m-dC were added to samples to facilitate detection and collection. The dC and 5 m-dC were collected in glass scintillation vials and dried on a vacuum concentrator. The samples were dissolved in water and mixed thoroughly with 10 mL of scintillation fluid. The $^{14}$C and $^{3}$H radiation levels in both dC and 5 m-dC from each reaction were measured by LSC (five or more cycles). 14C-labeled dC nucleoside was used to standardize the scintillation channel energy crossover with $^{3}$H in the low-energy range of 0-25 kiloelectron volts. Specific counts of the $^{14}$C and $^{3}$H isotopes were calculated by using the observed counts in both channels and the crossover ratio.

During each KIE experiment, control reactions that convert 100% of the labeled species to product were also conducted. Complete reactions (f=1) were achieved by extended incubation periods (24 h) with additional enzyme. These reactions were used to confirm the purity of radiolabels in the substrate (f=0) and to detect any nonreactive labels.

Measurement of SAM KIEs. KIEs were measured by internal competition using a mixture of isotope-labeled (heavy) and remote-labeled (light) SAM substrates. $^{14}$C— and $^{3}$H-labeled SAM and nonlabeled 26-bp hemimethylated DNA substrate were incubated in 100-µt solutions with 20 mM Tris.HCl (pH 7.4), 100 mM KCl, and 1 mM DTT at 37° C. Methylation reactions were initiated by the addition of human DNMT1. Enzyme-free control reactions (n≥5) were incubated simultaneously to the enzyme reaction samples. Control samples quantitated the slow chemical degradation of SAM during the reaction and sample handling. Reactions were quenched by adding 20 µL of 0.5 mM cold SAM and 50 mM $H_2SO_4$, and were stored immediately at −80° C. until HPLC purification.

Remaining unreacted SAM substrate from each reaction and control sample was purified by HPLC in ammonium formate buffer. The ds-DNA was trapped on the C18 guard column and was not observed as a defined peak. The $^{14}$C and $^{3}$H counts in the purified SAM were measured by LSC. Experimental KIEs were calculated from the isotope ratios present in the unreacted SAM substrate.

Computational Methods. The general procedures previously established (16) were followed to perform QM computational TS analysis of DNMT1. All of the geometry optimizations and frequency calculations were performed with Gaussian 09. In the final QM models, the GS of SAM was simulated using a density functional theory [with M06-2X functional (34) and 6-31+G(d,p) basis set], and the GS of DNA-Cyt and the TS of the methyl transfer were simulated using a two-layer ONIOM method (35, 36) [M062X/6-31+G(d,p):PM6] as implemented in Gaussian 09. The calculated vibrational frequencies were scaled by 0.967 to reproduce the true vibrational zero-point energies (37) for calculations of theoretical KIEs in the ISOEFF program (21) at the experimental temperature (37° C.).

Results

Isotope Labeling of DNA and SAM as DNMT1 Substrates. A library of six hemimethylated DNA and eight SAM substrates with site-specific isotope labels was synthesized to measure the respective KIEs. The isotopic labels were placed in chemical bond positions such that all atoms directly involved in the chemical steps of DNMT1-catalyzed reaction were represented. Six isotopically labeled dCTPs were prepared as the building blocks for the DNA substrates [5-$^{2}$H, 5'-$^{14}$C]-, [5-$^{13}$C, 5'-$^{14}$C]-, [6-$^{3}$H]-, [6-$^{14}$C]-, [5'-$^{3}$H$_2$]-, and [5'-$^{14}$C]-dCTPs through coupled reactions using up to 14 different enzymes (18). Each isotopically labeled dCTP was incorporated into a 26-bp DNA by in vitro replication using Klenow fragment extension (FIG. 2 A-C). The DNA molecules synthesized as labeled reactants all contained one hemimethylated CpG site, in which the unmethylated 2'-deoxycytidine (dC) residue is enriched with specific isotopes. This substrate design provides a single methylation site per DNA for methyltransferase; therefore, the observed KIEs are not complicated by processive DNA methylations. In addition, eight species of isotopically labeled SAM substrates were synthesized enzymatically from labeled ATP and methionine using SAM synthetase, including [Me-$^{13}$C, 8-$^{14}$C]-, [Me-$^{14}$C]-, [Me-$^{3}$H$_3$]-, [5'-$^{14}$C]-, [5'-$^{3}$H$_2$]-, [$^{36}$S, 8-$^{14}$C]-, [1'-$^{3}$H]-, and [8-$^{14}$C]-SAMs. The $^{36}$S-labeled SAM was synthesized from elemental $^{36}$S (19). The percentages of enrichment for stable heavy isotopes (i.e., $^{2}$H, $^{13}$C, $^{36}$S) in the isotopically labeled reactants were measured by MS.

Figure 1B:
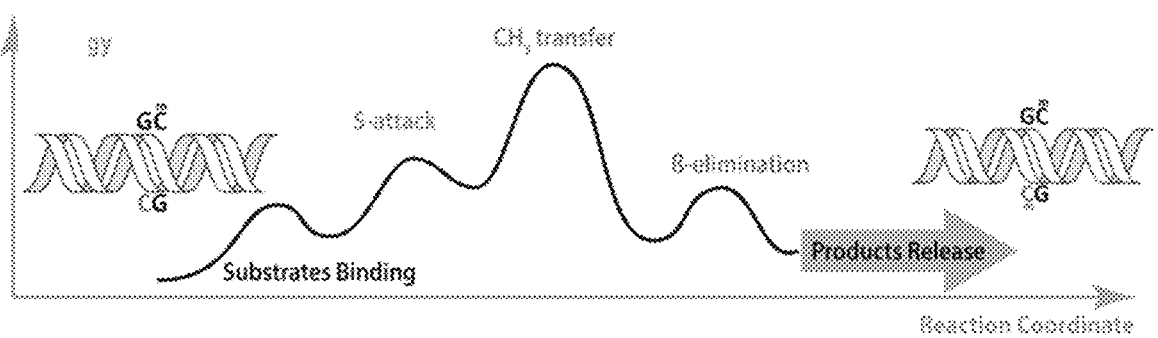

DNA and SAM Show Low Substrate Commitments in Vitro. In enzymatic reactions, the rate of chemical bond changes can be similar to the rates of substrate binding and product release. These rate similarities (called commitment factors) can obscure the values of the intrinsic chemical isotope effects and must be quantitated to permit calculation of intrinsic isotope effects. The forward commitment factor ($C_f$) values for DNA and SAM were measured by isotope trapping experiments. These experiments used pulse-chase analysis to trace radiolabeled product formation over the course of the reaction. The $C_f$ values for DNA and SAM bound to DNMT1 were found to be small and insignificant (0.016 and 0.0013, respectively). The small $C_f$ values establish that DNA and SAM bind to and release from DNMT1 63 and 770 times, respectively, before each catalytic turnover and are not highly committed to the chemical steps. Small $C_f$ values demonstrate that DNMT1-catalyzed methyl transfer is much slower than substrate binding and release steps. DNA binding requires Cyt base-flipping by DNMT1, and with dsDNA, multiple excursions into the catalytic site are required to achieve the proper catalytic site geometry for methylation. As a result of small $C_f$ values, the experimental KIE values are not significantly reduced by the $C_f$s and are within experimental error of intrinsic KIEs reporting on the rate-limiting chemical step(s) (FIG. 1B). The measured $C_f$ values are indicative of the behavior for isolated DNMT1 in vitro. The processivity of DNMT1 may increase in the context of nuclear DNA replication machinery, where DNMT1 is part of a multiprotein complex at the replication foci.

Figure 3:
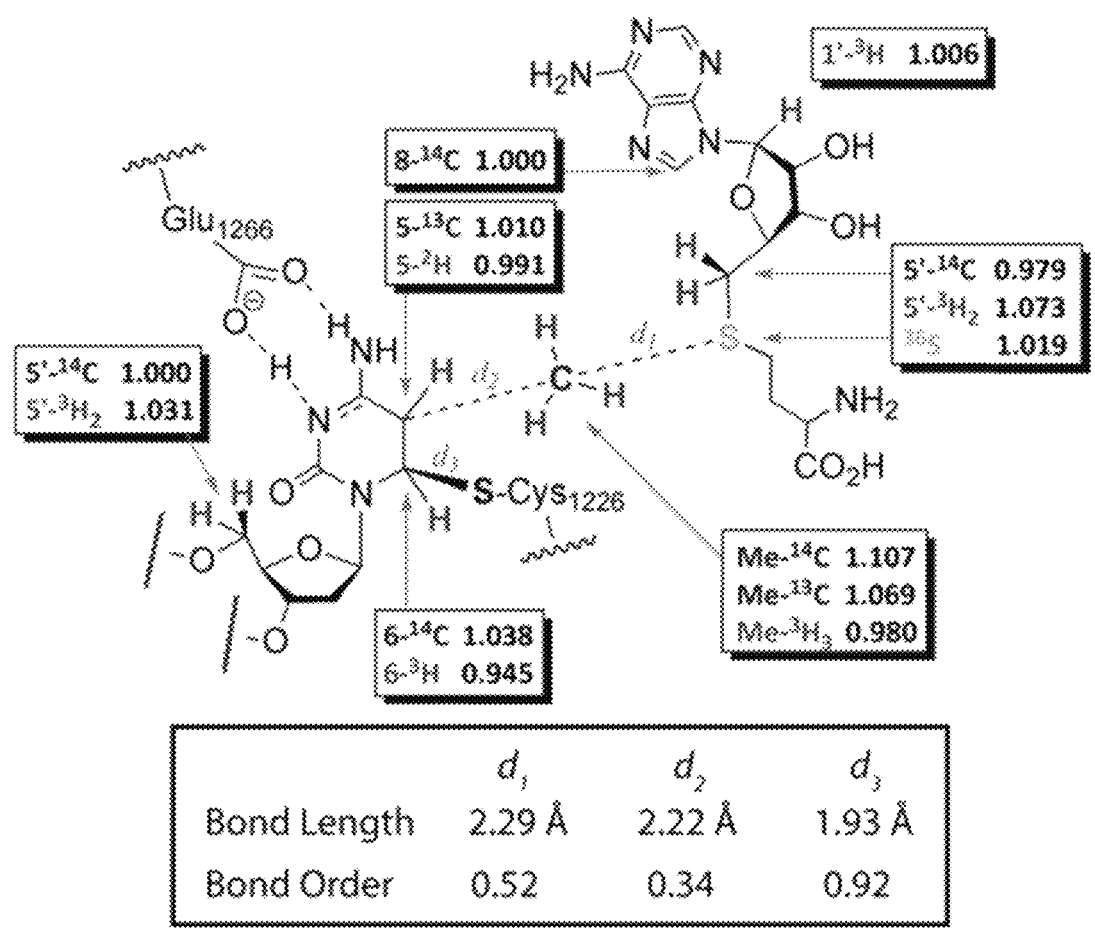
FIG. 3. Intrinsic KIEs and TS bonds for DNMT1-catalyzed DNA methylation. [5'-$^{14}$C] on DNA and [8-$^{14}$C] on SAM are remote control labels (KIE=1.000) for the substrates. Bond distances and bond orders are listed for the final ONIOM model of DNMT1 TS (FIG. 5): $d_1$ and $d_2$ are the bond distances from the Me-C to its donor and acceptor, and $d_3$ is the bond distance between the Cys sulfur and C6. The bond orders of $d_1$, $d_2$, and $d_3$ establish that the CH$_3$ transfer occurs while the C6-S bond is nearly complete (FIG. 1A).

Ten KIEs at Nine Atomic Positions Define the TS Parameters. Ten KIEs were measured at nine atomic positions in experiments to determine the rate-limiting TS of DNMT1-catalyzed DNA methylation (FIG. 3). Competitive assays with light and heavy substrates in the same reaction give high experimental accuracy (Table 1). The KIEs were determined by the change in isotope ratios traced by $^{3}$H or $^{14}$C, comparing the initial substrate with the residual substrate after DNMT1 conversion. KIEs for SAM were directly measured by isotopic depletion of the SAM substrate (Eq. 1), where f is the fraction of conversion and $R_s$ and $R_0$ are the isotope ratios found in the remaining substrate and the initial substrate. Control reactions without DNMT1 corrected for the spontaneous decomposition of SAM (20) during reactions. Cyt KIEs from DNA were obtained by resolution of isotopes in hemi-(substrate) and fully methylated (product) DNAs following hydrolysis to dC and 5-methyl-2'-deoxycytidine (5 m-dC) and separation by HPLC (FIG. 2D). The $^{3}$H and $^{14}$C isotopes in dC and 5 m-dC originated from the unreacted substrate and the fully methylated product, respectively:

$$KIE = \frac{\log(1-f)}{\log[(1-f)R_s/R_0]}. \quad [1]$$

Intrinsic KIEs report on the chemical structure of the dominant TS for DNMT1. The KIEs from the methyl carbon (Me-C) and sulfur of SAM report directly on the extent of methyl transfer to C5 of Cyt at the TS. The KIEs of [Me-$^{14}$C] (1.107), [Me-$^{13}$C] (1.069), and [$^{36}$S] (1.019) for SAM are near theoretical limits for their respective isotopic masses and establish a TS dominated by the methyl transfer step (FIG. 1B). In addition, the relatively large [6-$^{14}$C] Cyt KIE (1.038) and inverse [6-$^3$H] Cyt KIE (0.945) establish the sp$^3$ (tetrahedrally coordinated) character at C6 of Cyt, demonstrating the presence of a covalent bond between the Cys$^{1226}$ thiol and Cyt C6 at the TS. The 10 experimental KIEs provide a comprehensive dataset for resolving the DNMT1 kinetic mechanism and rate-limiting TS at subangstrom resolution.

Figures 4A, 4B, 4C:
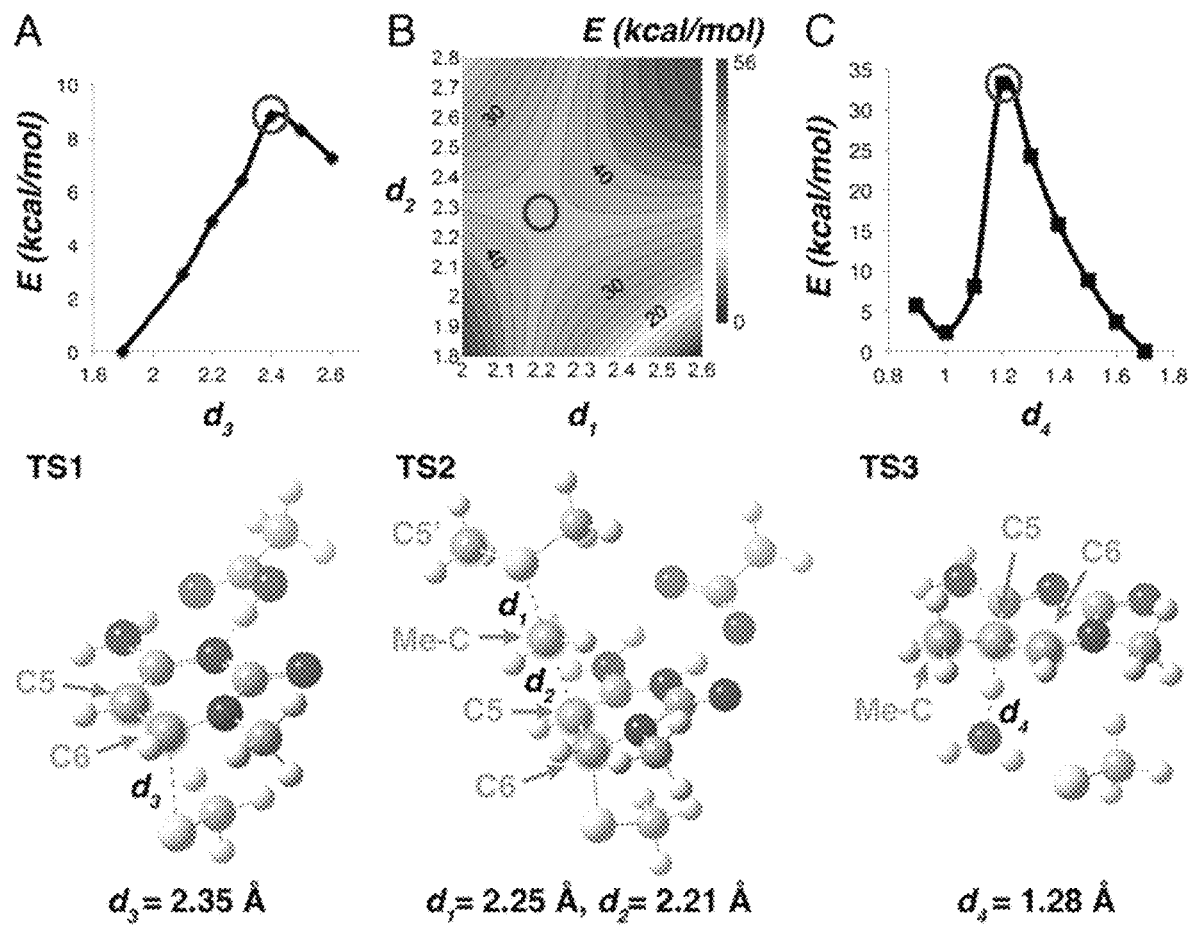
FIG. 4A-4C. Simple models used to predict KIEs for each chemical step. The models included a methane thiolate to mimic the Cys1226 residue, acetic acid to mimic the Glu1266 residue, and a water molecule as the proton acceptor in the third step. The potential energy (E) surface of each step was scanned by varying the bond distance(s) that drive the chemical reaction: $d_3$ is the C6-S distance between Cyt C6 and Cys1226 S atoms (A); $d_1$ is the distance between the Me-C and sulfur of SAM, and $d_2$ is the distance between the Me-C and C5 of Cyt (B); and $d_4$ is the distance between the water oxygen and the H5 of Cyt (C). The structures indicated by the circles in the energy plots (Top) were subsequently optimized as first-order saddle points to obtain the TS structures (Bottom) for each chemical step. The KIEs predicted for these theoretical TS structures are listed in Table 1.
Figure 5:
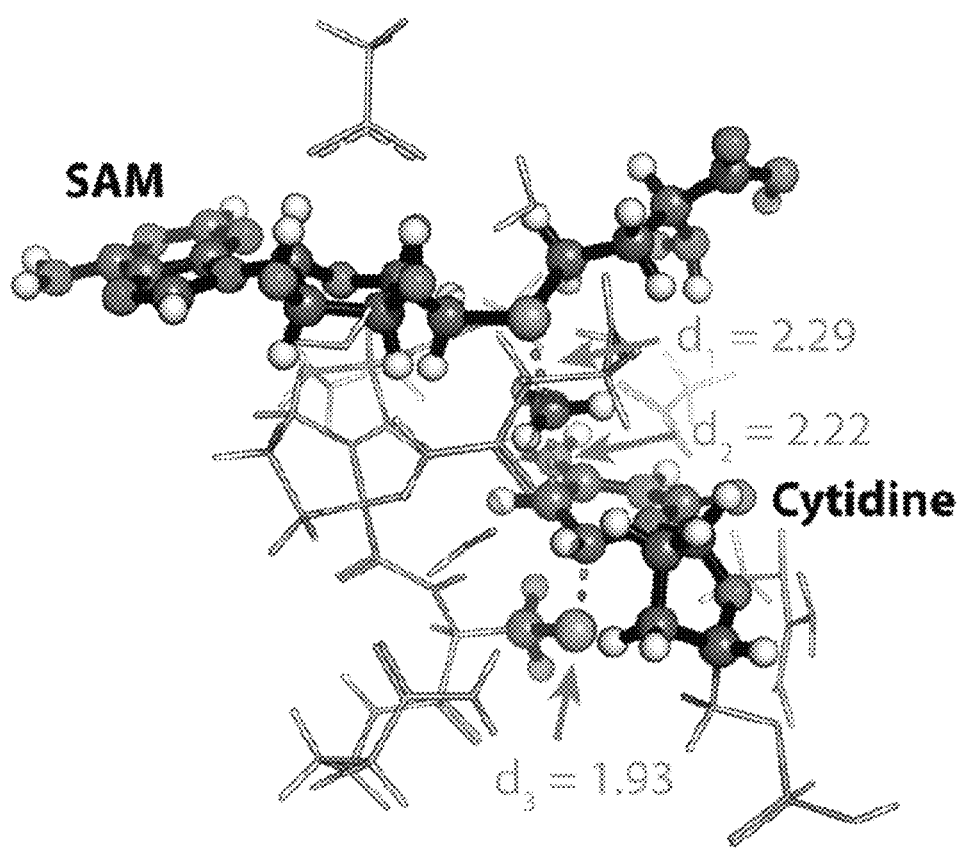
FIG. 5. Structure of the DNMT1 TS. TS of DNMT1 solved by QM predictions, in agreement with experimental KIEs. Electrostatic potential surface (ESPS) were calculated for this TS structure.

Methyl Transfer Is the Rate-Limiting Chemical Step. A quantitative demonstration of the TS for the DNMT1 reaction was obtained by comparing experimental KIEs with computationally predicted KIEs for each chemical TS as the highest barrier on the reaction coordinate, namely, the Cys1226 attack, methyl transfer, and β-elimination (TS1, TS2, and TS3 in FIGS. 1 and 4). Theoretical KIEs were predicted according to the Bigeleisen equations using ISO-EFF (21), based on vibrational frequencies calculated for the ground state (GS) and TS structures optimized in Gaussian 09 (22). β-Elimination (TS3) has been proposed as the rate-limiting step for bacterial M.HhaI methyltransferase by QM/MM and MD simulations (12). For human DNMT1, if TS3 were the highest barrier preceded by reversible steps, the [5-$^2$H]Cyt would show a large normal KIE, predicted to be 4.036, and the Me-C (Me-$^{13}$C and Me-$^{14}$C) KIEs would be slightly inverse (TS3 column in Table 1). These predictions contradict experimental KIEs (FIG. 3); therefore, the β-elimination step cannot be rate-limiting. Similarly, if Cys1226 attack were rate-limiting, the largest KIE would be observed on [6-$^{14}$C]Cyt, whereas Me-C KIEs would be in unity, because those atoms are not involved in the Cys1226 attack step (TS1 column in Table 1). The KIEs predicted for the methyl transfer step are consistent with experimental KIEs (TS2 column in Table 1), confirming that methyl transfer is rate-limiting for DNMT1. Small deviations from theory are observed for α- and β-secondary hydrogen KIEs. Secondary hydrogen KIEs often involve contributions from binding isotope effects (BIEs) arising from changes in the bonding environments for the free and enzyme-bound substrates. The vibrational modes altered by these binding environments are not captured in the simple models (FIG. 4). Gaussian's ONIOM method was used to account for changes in the bonding environments (FIG. 5).

TS Structure Reveals Stepwise DNMT1 Catalysis and Symmetrical Nucleophilic Substitution Methyl Transfer. A subangstrom structure of the DNMT1 TS was obtained by including close-contact protein residues and water molecules from the DNMT1 catalytic site (FIG. 5). A TS structure that reproduced experimental KIEs was optimized without applying geometry constraints (column of theoretical KIEs using ONIOM in Table 1). This TS structure has a single imaginary frequency corresponding to methyl transfer in the reaction coordinate.

The TS of DNMT1 is defined by 10 experimental and QM-predicted KIEs, and provides excellent agreement for all primary atomic positions (Table 1). Both the GS of DNA-Cyt and the TS of DNMT1 were simulated by a two-layer ONIOM [M062X/6-31+G(d,p):PM6] method. Cyt in free DNA was modeled by double-strand TCG (thymine, cytosine, guanine) base stacking (23, 24), and DNMT1 TS was simulated by a model, including SAM, deoxycytidine 5'-monophosphate, eight DNMT1 residues, and three water molecules (196 atoms in total). Heavy atoms ([5-$^{14}$C]- and [6-$^{14}$C]-Cyt and [Me-$^{13}$C]-, [Me-$^{14}$C]-, and [$^{36}$S]-SAM) KIEs are only influenced by covalent bond changes, not by binding interactions, and therefore reliably define the TS geometry. The final TS model describes a near-symmetrical nucleophilic substitution (S$_N$2) TS for methyl transfer from the sulfur of SAM to C5 of Cyt of DNA. The bond distances from the Me-C to its donor and acceptor are d1=2.29 Å and d2=2.22 Å, with bond orders of 0.52 and 0.34, respectively. It is significant that these bond orders sum to less than 1.0 (0.86), indicating a loose (noncompressed) nucleophilic substitution reaction.

The DNMT1 methyl transfer TS involves a nearly complete covalent bond between the sulfur of Cys1226 and C6 with a bond distance of d3=1.93 Å and a bond order of 0.92. This TS structure is consistent with the stepwise mechanism depicted in FIG. 1, where methyl transfer occurs after formation of the covalent bond between the sulfur of Cys1226 and C6 and the methyl transfer step is chemically rate-limiting for DNMT1. These features of human DNMT1 are different from the mechanism of M.HhaI DNMT suggested from previous QM/MM simulations (11, 12).

Natural bond orbital analysis (22) of the methyl transfer TS permits construction of an electrostatic potential surface that visualizes the polarity, electronegativity, and bond characteristics of the TS. The TS of DNMT1 shows a distribution of the positive charge in the direction of methyl transfer, originating from the SAM sulfonium ion and extending toward the Cyt ring. The electrostatic character of the reaction center at the TS is different from the SAM substrate and sinefungin, a relatively weak binding analog of SAM.

Discussion

DNA Cyt methyltransferases have been identified in organisms ranging from bacteria to humans. The bacterial enzymes perform DNA methylation to protect themselves from endogenous restriction enzymes. In mammalian cells, DNMTs have extensive N-terminal regulatory domains in addition to the catalytic domain, and the genomic methylation patterns are generally associated with gene regulation. Despite their differences in overall size and biological roles, the bacterial enzymes (exemplified by M.HhaI methyltransferase) and mammalian DNMT1 share a conserved set of active site residues in the covalent complex (4). They also catalyze similar steps (FIG. 1A) for methylating Cyt, including Cyt base-flipping, Cys attack on C6, methyl transfer, and β-elimination. Although previous computational studies predicted the β-elimination to be rate-limiting for M.HhaI (12), the present experimental KIEs, together with QM analysis on DNMT1, demonstrate a mechanism where methyl transfer has the largest energy barrier among the chemical steps.

The TS formed by DNMT1, resolved here to subangstrom resolution, is the most complex enzyme system yet analyzed by a combination of KIEs and quantum chemistry. In this TS structure, a nearly full bond is formed between Cys1226 and Cyt C6 (bond order=0.92), whereas the sum of two bond orders on the methyl transfer path (d1 and d2) is less than 1 (0.86). Whether the Cys attack occurs before or simultaneously with methyl transfer during DNMT catalysis has been debated. These results suggest a stepwise mechanism for DNMT1, where the Cys attack is not fully synchronized with methyl transfer. This evidence is also believed to be the first combined experimental and computational evidence that addresses concertedness for a DNMT.

Compression of the methyl donor and acceptor at the TS has been proposed for catechol-O-methyltransferases (COMTs) (25, 26), but has been disputed in theoretical studies (27, 28). In the DNMT1 TS, bond orders on the methyl transfer path (d1 and d2) sum to less than 1, indicating a loose $S_N2$ substitution for the methyl transfer, in contrast to a compression-type TS claimed on COMT (25, 26). This discrepancy is not entirely surprising, given the major differences in the methyl acceptors and the catalytic mechanisms involved. Comparative results from COMT and DNMT1 suggest that diverse TS mechanisms exist among the SAM-dependent methyltransferases.

Inhibitors of human DNMT have been used in cancer therapy (29), because elevated CpG methylation in tumor repressors can result in carcinogenesis. However, all U.S. Food and Drug Administration-approved DNMT inhibitors are cytotoxic and mutagenic. Those inhibitors (i.e., 5-azacytidine, 5-aza-deoxycytidine) promote DNA demethylation by incorporation into host DNA to form covalent adducts between DNMTs and DNA. Other DNMT inhibitors have been identified from chemical library screening, but they often lack specificity against DNMTs (30). The subangstrom geometry and electrostatics details of the DNMT1 TS described here will assist the design of mechanism-based TS analog inhibitors for DNMT1. Solving the TS of DNMT1 provides proof of concept to gain mechanistic and chemical insights into complex enzyme reactions involved in epigenetic control (31, 32) and other macromolecular modifications.

TABLE 1

Experimental and theoretical KIEs

| Position | Experiment V/K KIEs* | KIEs predicted from simple model analysis† | | | Theoretical KIEs using ONIOM‡ |
|---|---|---|---|---|---|
| | | TS1 | TS2 | TS3 | |
| 5-$^{13}$C | 1.010 ± 0.004 | 1.007 | 1.013 | 0.997 | 1.009 |
| 5-$^2$H | 0.991 ± 0.005§ | 1.048 | 0.973 | 4.036 | 0.955 |
| 6-$^{14}$C | 1.038 ± 0.005 | 1.073 | 1.029 | 0.994 | 1.036 |
| 6-$^3$H | 0.94 ± 0.01 | 0.971 | 0.874 | 1.066 | 0.901 |
| Me—$^{14}$C | 1.107 ± 0.006 | ND← | 1.106 | 0.980 | 1.110 |
| Me—$^{13}$C | 1.07 ± 0.01 | ND | 1.055 | 0.989 | 1.057 |
| Me—$^3$H$_3$ | 0.980 ± 0.006 | ND | 0.814 | 0.993 | 0.964 |
| 5'-$^{14}$C | 0.979 ± 0.008 | ND | 1.030 | ND← | 0.996 |
| 5'-$^3$H$_2$ | 1.073 ± 0.003 | ND | 1.318 | ND | 1.066 |
| $^{36}$S | 1.019 ± 0.006 | ND | 1.016 | ND | 1.017 |

ND, not determined; V/K, maximum catalytic rate/Michaelis constant.
* Intrinsic KIEs measured experimentally, represented by an average ± SD.
†KIEs predicted with the traditional TS theory, based on the vibrational differences between the GS structures and TS structures of each chemical step (FIG. 4).
‡KIEs predicted for the methyl transfer TS structure by ONIOM (Gaussian's "our own N-layered integrated molecular orbital and molecular mechanics") simulations (FIG. 5). No geometry constraints were necessary in the final model to reach the agreement with experimental KIEs.
§Representative primary data from six individual experiments, with the values 0.98798, 0.98422, 0.99363, 0.99452, 0.99435, and 0.98974, were used to calculate the experimental KIE for 5-$^2$H shown in the table.
←These atoms do not participate in this chemical step and will not contribute KIE values.

REFERENCES

1. Bird A (2002) DNA methylation patterns and epigenetic memory. Genes Dev 16(1):6-21.
2. Jones P A, Baylin S B (2002) The fundamental role of epigenetic events in cancer. Nat Rev Genet 3(6):415-428.
3. Bestor T H (2000) The DNA methyltransferases of mammals. Hum Mol Genet 9(16):2395-2402.
4. Song J, Teplova M, Ishibe-Murakami S, Patel D J (2012) Structure-based mechanistic insights into DNMT1-mediated maintenance DNA methylation. Science 335(6069): 709-712.
5. Takeshita K, et al. (2011) Structural insight into maintenance methylation by mouse DNA methyltransferase 1 (Dnmt1). Proc Natl Acad Sci USA 108(22):9055-9059.
6. Song J, Rechkoblit O, Bestor T H, Patel D J (2011) Structure of DNMT1-DNA complex reveals a role for autoinhibition in maintenance DNA methylation. Science 331(6020):1036-1040.
7. Bashtrykov P, et al. (2012) Specificity of Dnmt1 for methylation of hemimethylated CpG sites resides in its catalytic domain. Chem Biol 19(5):572-578.
8. Wu J C, Santi D V (1987) Kinetic and catalytic mechanism of HhaI methyltransferase. J Biol Chem 262(10): 4778-4786.
9. Chen L, Macmillan A M, Verdine G L (1993) Mutational separation of DNA-binding from catalysis in a DNA cytosine methyltransferase. J Am Chem Soc 115(12): 5318-5319.
10. Klimasauskas S, Kumar S, Roberts R J, Cheng X (1994) HhaI methyltransferase flips its target base out of the DNA helix. Cell 76(2):357-369.
11. Zhang X, Bruice T C (2006) The mechanism of M.HhaI DNA C5 cytosine methyltransferase enzyme: A quantum mechanics/molecular mechanics approach. Proc Natl Acad Sci USA 103(16):6148-6153.
12. Yang J, Lior-Hoffmann L, Wang S, Zhang Y, Broyde S (2013) DNA cytosine methylation: Structural and thermodynamic characterization of the epigenetic marking mechanism. Biochemistry 52(16):2828-2838.
13. Pauling L (1946) Molecular architecture and biological reactions. Chem Eng News 24(10): 1375-1377.
14. Pearson A D, et al. (2015) Transition states. Trapping a transition state in a computationally designed protein bottle. Science 347(6224):863-867.
15. Cleland W W (1995) Isotope effects: Determination of enzyme transition state structure. Methods Enzymol 249: 341-373.
16. Schramm V L (2011) Enzymatic transition states, transition-state analogs, dynamics, thermodynamics, and lifetimes. Annu Rev Biochem 80:703-732.
17. Hiller D A, Singh V, Zhong M, Strobel S A (2011) A two-step chemical mechanism for ribosome-catalysed peptide bond formation. Nature 476(7359):236-239.
18. Scott L G, Tolbert T J, Williamson J R (2000) Preparation of specifically 2H—and 13C—labeled ribonucleotides. Methods Enzymol 317:18-38.
19. Poulin M B, Du Q, Schramm V L (2015) Chemoenzymatic Synthesis of (36)S Isotopologues of Methionine and S-Adenosyl-L-methionine. J Org Chem 80(10):5344-5347.
20. Wu S E, Huskey W P, Borchardt R T, Schowen R L (1983) Chiral instability at sulfur of S-adenosylmethionine. Biochemistry 22(12):2828-2832.
21. Anisimov V, Paneth P (1999) ISOEFF98. A program for studies of isotope effects using Hessian modifications. J Math Chem 26(1-3):75-86.
22. Frisch M J, et al. (2009) Gaussian 09 (Gaussian, Inc., Wallingford, Conn.).
23. Cerón-Carrasco J P, et al. (2011) Combined effect of stacking and solvation on the spontaneous mutation in DNA. Phys Chem Chem Phys 13(32):14584-14589.
24. Galano A, Alvarez-Idaboy J R (2012) On the evolution of one-electron-oxidized deoxyguanosine in damaged DNA under physiological conditions: A DFT and ONIOM 25. Hegazi M F, Borchardt R T, Schowen R L (1979) α-Deuterium and carbon-13 isotope effects for methyl transfer catalyzed by catechol O-methyltransferase. $S_N2$-like transition state. J Am Chem Soc 101(15):4359-4365.
26. Zhang J, Klinman J P (2011) Enzymatic methyl transfer: Role of an active site residue in generating active site compaction that correlates with catalytic efficiency. J Am Chem Soc 133(43):17134-17137.
27. Ruggiero G D, Williams I H, Roca M, Moliner V, Tuñón I (2004) QM/MM determination of kinetic isotope effects for COMT-catalyzed methyl transfer does not support compression hypothesis. J Am Chem Soc 126(28):8634-8635.
28. Lameira J, Bora R P, Chu Z T, Warshel A (2015) Methyltransferases do not work by compression, cratic, or desolvation effects, but by electrostatic preorganization. Proteins 83(2):318-330.
29. Christman J K (2002) 5-Azacytidine and 5-aza-2'-deoxycytidine as inhibitors of DNA methylation: Mechanistic studies and their implications for cancer therapy. Oncogene 21(35):5483-5495.
30. Gros C, et al. (2012) DNA methylation inhibitors in cancer: Recent and future approaches. Biochimie 94(11): 2280-2296.
31. Baylin S B, Jones P A (2011) A decade of exploring the cancer epigenome—biological and translational implications. Nat Rev Cancer 11(10):726-734.
32. Wigle T J, Copeland R A (2013) Drugging the human methylome: An emerging modality for reversible control of aberrant gene transcription. Curr Opin Chem Biol 17(3): 369-378.
33. Hemeon I, Gutierrez J A, Ho M C, Schramm V L (2011) Characterizing DNA methyltransferases with an ultrasensitive luciferase-linked continuous assay. Anal Chem 83(12):4996-5004.
34. Zhao Y, Truhlar D (2008) The M06 suite of density functionals for main group thermochemistry, thermochemical kinetics, noncovalent interactions, excited states, and transition elements: Two new functionals and systematic testing of four M06-class functionals and 12 other functionals. Theor Chem Acc 120(1-3):215-241.
35. Dapprich S, Komáromi I, Byun K S, Morokuma K, Frisch M J (1999) A new ONIOM implementation in Gaussian 98. Part I. The calculation of energies, gradients, vibrational frequencies and electric field derivatives. Journal of Molecular Structure: THEOCHEM 461-462:1-21.
36. Vreven T, Morokuma K, Farkas O, Schlegel H B, Frisch M J (2003) Geometry optimization with QM/MM, ONIOM, and other combined methods. I. Microiterations and constraints. J Comput Chem 24(6):760-769.
37. Alecu I M, Zheng J, Zhao Y, Truhlar D G (2010) Computational Thermochemistry: Scale Factor Databases and Scale Factors for Vibrational Frequencies Obtained from Electronic Model Chemistries. J Chem Theory Comput 6(9):2872-2887.
38. Bagdassarian, C. K., Schramm, V. L., and Schwartz, S. D. (1996) Molecular electrostatic potential analysis for enzymatic substrates, competitive inhibitors and transition-state inhibitors, J. Am. Chem. Soc. 118, 8825-8836.

What is claimed is:

1. A method of detecting, screening for or designing an inhibitor of human DNA methyltransferase 1 (DNMT1), the method comprising the steps of:
(i) measuring kinetic isotope effects on DNMT1-catalyzed methylation of hemimethylated DNA to obtain the DNMT1 transition state structure,
wherein the DNMT1 transition state comprises the structure

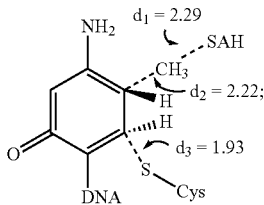

(ii) determining the molecular electrostatic potential at the van der Waals surface computed from a wave function of the DNMT1 transition state and a geometric atomic volume of the DNMT1 transition state;
(iii) obtaining a chemically stable compound that resembles the molecular electrostatic potential at the van der Waals surface computed from the wave function of the DNMT1 transition state and the geometric atomic volume of the DNMT1 transition state; and
(iv) testing the compound for inhibitory activity to DNMT1 by determining if the compound inhibits DNMT1-catalyzed methylation of hemimethylated DNA;
wherein the compound that inhibits DNMT1-catalyzed methylation of hemimethylated DNA is an inhibitor of DNMT1;
thereby detecting, screening for or designing an inhibitor of human DNA methyltransferase 1 (DNMT1).

2. The method of claim 1, wherein step (i) comprises measuring $^{14}C$ and $^{3}H$ radiation levels of mononucleosides digested from the DNA after the DNMT1-catalyzed methylation.

3. The method of claim 1, wherein step (i) comprises measuring $^{14}C$ and $^{3}H$ labelled and unreacted SAM substrate after the DNMT1-catalyzed methylation.

4. The method of claim 1, wherein step (i) comprises reacting $^{14}C$— and $^{3}H$-labeled hemimethylated DNA and nonlabeled SAM for the DNMT1-catalyzed methylation.

5. A computer-implemented method performed using a system comprising a non-transitory computer-readable medium coupled to one or more data processing apparatus having instructions stored thereon, the method comprising:
(i) determining a molecular electrostatic potential at the van der Waals surface computed from a wave function of a DNMT1 transition state and a geometric atomic volume of the DNMT1 transition state,
wherein the DNMT1 transition state comprises the structure

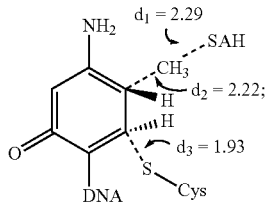

(ii) identifying from a library of compounds a chemically stable compound that resembles the molecular electrostatic potential at the van der Waals surface computed from the wave function of the DNMT1 transition state and the geometric atomic volume of the DNMT1 transition state;
wherein the chemically stable compound that resembles the molecular electrostatic potential at the van der Waals surface computed from the wave function of the DNMT1 transition state and the geometric atomic volume of the DNMT1 transition state is a putative inhibitor of DNMT1;
(iii) testing the putative inhibitor for inhibitory activity to DNMT1 by determining if the a putative inhibitor inhibits DNMT1-catalyzed methylation of hemimethylated DNA;
wherein the putative inhibitor that inhibits DNMT1-catalyzed methylation of hemimethylated DNA is an inhibitor of DNMT1.

* * * * *

SEQUENCE LISTING

```
<160> NUMBER OF SEQ ID NOS: 4

<210> SEQ ID NO 1
<211> LENGTH: 1616
<212> TYPE: PRT
<213> ORGANISM: Homo sapiens

<400> SEQUENCE: 1

Met Pro Ala Arg Thr Ala Pro Ala Arg Val Pro Thr Leu Ala Val Pro
1               5                   10                  15

Ala Ile Ser Leu Pro Asp Asp Val Arg Arg Arg Leu Lys Asp Leu Glu
            20                  25                  30

Arg Asp Ser Leu Thr Glu Lys Glu Cys Val Lys Glu Lys Leu Asn Leu
        35                  40                  45

Leu His Glu Phe Leu Gln Thr Glu Ile Lys Asn Gln Leu Cys Asp Leu
    50                  55                  60

Glu Thr Lys Leu Arg Lys Glu Glu Leu Ser Glu Glu Gly Tyr Leu Ala
65                  70                  75                  80

Lys Val Lys Ser Leu Leu Asn Lys Asp Leu Ser Leu Glu Asn Gly Ala
                85                  90                  95

His Ala Tyr Asn Arg Glu Val Asn Gly Arg Leu Glu Asn Gly Asn Gln
            100                 105                 110

Ala Arg Ser Glu Ala Arg Arg Val Gly Met Ala Asp Ala Asn Ser Pro
        115                 120                 125

Pro Lys Pro Leu Ser Lys Pro Arg Thr Pro Arg Arg Ser Lys Ser Asp
    130                 135                 140

Gly Glu Ala Lys Pro Glu Pro Ser Pro Ser Pro Arg Ile Thr Arg Lys
145                 150                 155                 160
```

-continued

```
Ser Thr Arg Gln Thr Thr Ile Thr Ser His Phe Ala Lys Gly Pro Ala
                165                 170                 175

Lys Arg Lys Pro Gln Glu Glu Ser Glu Arg Ala Lys Ser Asp Glu Ser
            180                 185                 190

Ile Lys Glu Glu Asp Lys Asp Gln Asp Glu Lys Arg Arg Arg Val Thr
        195                 200                 205

Ser Arg Glu Arg Val Ala Arg Pro Leu Pro Ala Glu Pro Glu Arg
210                 215                 220

Ala Lys Ser Gly Thr Arg Thr Glu Lys Glu Glu Arg Asp Glu Lys
225                 230                 235                 240

Glu Glu Lys Arg Leu Arg Ser Gln Thr Lys Glu Pro Thr Pro Lys Gln
                245                 250                 255

Lys Leu Lys Glu Glu Pro Asp Arg Glu Ala Arg Ala Gly Val Gln Ala
            260                 265                 270

Asp Glu Asp Glu Asp Gly Asp Glu Lys Asp Glu Lys Lys His Arg Ser
        275                 280                 285

Gln Pro Lys Asp Leu Ala Ala Lys Arg Pro Glu Glu Lys Glu Pro
            290                 295                 300

Glu Lys Val Asn Pro Gln Ile Ser Asp Glu Lys Asp Glu Asp Glu Lys
305                 310                 315                 320

Glu Glu Lys Arg Arg Lys Thr Thr Pro Lys Glu Pro Thr Glu Lys Lys
                325                 330                 335

Met Ala Arg Ala Lys Thr Val Met Asn Ser Lys Thr His Pro Pro Lys
                340                 345                 350

Cys Ile Gln Cys Gly Gln Tyr Leu Asp Asp Pro Asp Leu Lys Tyr Gly
                355                 360                 365

Gln His Pro Pro Asp Ala Val Asp Glu Pro Gln Met Leu Thr Asn Glu
        370                 375                 380

Lys Leu Ser Ile Phe Asp Ala Asn Glu Ser Gly Phe Glu Ser Tyr Glu
385                 390                 395                 400

Ala Leu Pro Gln His Lys Leu Thr Cys Phe Ser Val Tyr Cys Lys His
                405                 410                 415

Gly His Leu Cys Pro Ile Asp Thr Gly Leu Ile Glu Lys Asn Ile Glu
            420                 425                 430

Leu Phe Phe Ser Gly Ser Ala Lys Pro Ile Tyr Asp Asp Pro Ser
        435                 440                 445

Leu Glu Gly Gly Val Asn Gly Lys Asn Leu Gly Pro Ile Asn Glu Trp
        450                 455                 460

Trp Ile Thr Gly Phe Asp Gly Gly Glu Lys Ala Leu Ile Gly Phe Ser
465                 470                 475                 480

Thr Ser Phe Ala Glu Tyr Ile Leu Met Asp Pro Ser Pro Glu Tyr Ala
                485                 490                 495

Pro Ile Phe Gly Leu Met Gln Glu Lys Ile Tyr Ile Ser Lys Ile Val
            500                 505                 510

Val Glu Phe Leu Gln Ser Asn Ser Asp Ser Thr Tyr Glu Asp Leu Ile
        515                 520                 525

Asn Lys Ile Glu Thr Thr Val Pro Pro Ser Gly Leu Asn Leu Asn Arg
530                 535                 540

Phe Thr Glu Asp Ser Leu Leu Arg His Ala Gln Phe Val Val Glu Gln
545                 550                 555                 560

Val Glu Ser Tyr Asp Glu Ala Gly Asp Ser Asp Glu Gln Pro Ile Phe
                565                 570                 575

Leu Thr Pro Cys Met Arg Asp Leu Ile Lys Leu Ala Gly Val Thr Leu
```

```
              580                 585                 590
    Gly Gln Arg Arg Ala Gln Ala Arg Arg Gln Thr Ile Arg His Ser Thr
                    595                 600                 605
    Arg Glu Lys Asp Arg Gly Pro Thr Lys Ala Thr Thr Thr Lys Leu Val
                    610                 615                 620
    Tyr Gln Ile Phe Asp Thr Phe Phe Ala Glu Gln Ile Glu Lys Asp Asp
    625                 630                 635                 640
    Arg Glu Asp Lys Glu Asn Ala Phe Lys Arg Arg Cys Gly Val Cys
                        645                 650                 655
    Glu Val Cys Gln Gln Pro Glu Cys Gly Lys Cys Lys Ala Cys Lys Asp
                    660                 665                 670
    Met Val Lys Phe Gly Gly Ser Gly Arg Ser Lys Gln Ala Cys Gln Glu
                    675                 680                 685
    Arg Arg Cys Pro Asn Met Ala Met Lys Glu Ala Asp Asp Glu Glu
                    690                 695                 700
    Val Asp Asp Asn Ile Pro Glu Met Pro Ser Pro Lys Lys Met His Gln
    705                 710                 715                 720
    Gly Lys Lys Lys Lys Gln Asn Lys Asn Arg Ile Ser Trp Val Gly Glu
                        725                 730                 735
    Ala Val Lys Thr Asp Gly Lys Lys Ser Tyr Tyr Lys Lys Val Cys Ile
                    740                 745                 750
    Asp Ala Glu Thr Leu Glu Val Gly Asp Cys Val Ser Val Ile Pro Asp
                    755                 760                 765
    Asp Ser Ser Lys Pro Leu Tyr Leu Ala Arg Val Thr Ala Leu Trp Glu
    770                 775                 780
    Asp Ser Ser Asn Gly Gln Met Phe His Ala His Trp Phe Cys Ala Gly
    785                 790                 795                 800
    Thr Asp Thr Val Leu Gly Ala Thr Ser Asp Pro Leu Glu Leu Phe Leu
                    805                 810                 815
    Val Asp Glu Cys Glu Asp Met Gln Leu Ser Tyr Ile His Ser Lys Val
                    820                 825                 830
    Lys Val Ile Tyr Lys Ala Pro Ser Glu Asn Trp Ala Met Glu Gly Gly
                    835                 840                 845
    Met Asp Pro Glu Ser Leu Leu Glu Gly Asp Asp Gly Lys Thr Tyr Phe
    850                 855                 860
    Tyr Gln Leu Trp Tyr Asp Gln Asp Tyr Ala Arg Phe Glu Ser Pro Pro
    865                 870                 875                 880
    Lys Thr Gln Pro Thr Glu Asp Asn Lys Phe Lys Phe Cys Val Ser Cys
                        885                 890                 895
    Ala Arg Leu Ala Glu Met Arg Gln Lys Glu Ile Pro Arg Val Leu Glu
                    900                 905                 910
    Gln Leu Glu Asp Leu Asp Ser Arg Val Leu Tyr Tyr Ser Ala Thr Lys
                    915                 920                 925
    Asn Gly Ile Leu Tyr Arg Val Gly Asp Gly Val Tyr Leu Pro Pro Glu
                    930                 935                 940
    Ala Phe Thr Phe Asn Ile Lys Leu Ser Ser Pro Val Lys Arg Pro Arg
    945                 950                 955                 960
    Lys Glu Pro Val Asp Glu Asp Leu Tyr Pro Glu His Tyr Arg Lys Tyr
                        965                 970                 975
    Ser Asp Tyr Ile Lys Gly Ser Asn Leu Asp Ala Pro Glu Pro Tyr Arg
                    980                 985                 990
    Ile Gly Arg Ile Lys Glu Ile Phe  Cys Pro Lys Lys Ser  Asn Gly Arg
                    995                     1000                1005
```

-continued

Pro Asn Glu Thr Asp Ile Lys Ile Arg Val Asn Lys Phe Tyr Arg
1010              1015              1020

Pro Glu Asn Thr His Lys Ser Thr Pro Ala Ser Tyr His Ala Asp
1025              1030              1035

Ile Asn Leu Leu Tyr Trp Ser Asp Glu Glu Ala Val Val Asp Phe
1040              1045              1050

Lys Ala Val Gln Gly Arg Cys Thr Val Glu Tyr Gly Glu Asp Leu
1055              1060              1065

Pro Glu Cys Val Gln Val Tyr Ser Met Gly Gly Pro Asn Arg Phe
1070              1075              1080

Tyr Phe Leu Glu Ala Tyr Asn Ala Lys Ser Lys Ser Phe Glu Asp
1085              1090              1095

Pro Pro Asn His Ala Arg Ser Pro Gly Asn Lys Gly Lys Gly Lys
1100              1105              1110

Gly Lys Gly Lys Gly Lys Pro Lys Ser Gln Ala Cys Glu Pro Ser
1115              1120              1125

Glu Pro Glu Ile Glu Ile Lys Leu Pro Lys Leu Arg Thr Leu Asp
1130              1135              1140

Val Phe Ser Gly Cys Gly Gly Leu Ser Glu Gly Phe His Gln Ala
1145              1150              1155

Gly Ile Ser Asp Thr Leu Trp Ala Ile Glu Met Trp Asp Pro Ala
1160              1165              1170

Ala Gln Ala Phe Arg Leu Asn Asn Pro Gly Ser Thr Val Phe Thr
1175              1180              1185

Glu Asp Cys Asn Ile Leu Leu Lys Leu Val Met Ala Gly Glu Thr
1190              1195              1200

Thr Asn Ser Arg Gly Gln Arg Leu Pro Gln Lys Gly Asp Val Glu
1205              1210              1215

Met Leu Cys Gly Gly Pro Pro Cys Gln Gly Phe Ser Gly Met Asn
1220              1225              1230

Arg Phe Asn Ser Arg Thr Tyr Ser Lys Phe Lys Asn Ser Leu Val
1235              1240              1245

Val Ser Phe Leu Ser Tyr Cys Asp Tyr Tyr Arg Pro Arg Phe Phe
1250              1255              1260

Leu Leu Glu Asn Val Arg Asn Phe Val Ser Phe Lys Arg Ser Met
1265              1270              1275

Val Leu Lys Leu Thr Leu Arg Cys Leu Val Arg Met Gly Tyr Gln
1280              1285              1290

Cys Thr Phe Gly Val Leu Gln Ala Gly Gln Tyr Gly Val Ala Gln
1295              1300              1305

Thr Arg Arg Arg Ala Ile Ile Leu Ala Ala Ala Pro Gly Glu Lys
1310              1315              1320

Leu Pro Leu Phe Pro Glu Pro Leu His Val Phe Ala Pro Arg Ala
1325              1330              1335

Cys Gln Leu Ser Val Val Val Asp Asp Lys Lys Phe Val Ser Asn
1340              1345              1350

Ile Thr Arg Leu Ser Ser Gly Pro Phe Arg Thr Ile Thr Val Arg
1355              1360              1365

Asp Thr Met Ser Asp Leu Pro Glu Val Arg Asn Gly Ala Ser Ala
1370              1375              1380

Leu Glu Ile Ser Tyr Asn Gly Glu Pro Gln Ser Trp Phe Gln Arg
1385              1390              1395

```
Gln Leu Arg Gly Ala Gln Tyr Gln Pro Ile Leu Arg Asp His Ile
    1400            1405                1410

Cys Lys Asp Met Ser Ala Leu Val Ala Ala Arg Met Arg His Ile
    1415            1420                1425

Pro Leu Ala Pro Gly Ser Asp Trp Arg Asp Leu Pro Asn Ile Glu
    1430            1435                1440

Val Arg Leu Ser Asp Gly Thr Met Ala Arg Lys Leu Arg Tyr Thr
    1445            1450                1455

His His Asp Arg Lys Asn Gly Arg Ser Ser Gly Ala Leu Arg
    1460            1465                1470

Gly Val Cys Ser Cys Val Glu Ala Gly Lys Ala Cys Asp Pro Ala
    1475            1480                1485

Ala Arg Gln Phe Asn Thr Leu Ile Pro Trp Cys Leu Pro His Thr
    1490            1495                1500

Gly Asn Arg His Asn His Trp Ala Gly Leu Tyr Gly Arg Leu Glu
    1505            1510                1515

Trp Asp Gly Phe Phe Ser Thr Thr Val Thr Asn Pro Glu Pro Met
    1520            1525                1530

Gly Lys Gln Gly Arg Val Leu His Pro Glu Gln His Arg Val Val
    1535            1540                1545

Ser Val Arg Glu Cys Ala Arg Ser Gln Gly Phe Pro Asp Thr Tyr
    1550            1555                1560

Arg Leu Phe Gly Asn Ile Leu Asp Lys His Arg Gln Val Gly Asn
    1565            1570                1575

Ala Val Pro Pro Pro Leu Ala Lys Ala Ile Gly Leu Glu Ile Lys
    1580            1585                1590

Leu Cys Met Leu Ala Lys Ala Arg Glu Ser Ala Ser Ala Lys Ile
    1595            1600                1605

Lys Glu Glu Glu Ala Ala Lys Asp
    1610            1615

<210> SEQ ID NO 2
<211> LENGTH: 12
<212> TYPE: DNA
<213> ORGANISM: Artificial Sequence
<220> FEATURE:
<223> OTHER INFORMATION: tool for KIE measurement on DNMT1

<400> SEQUENCE: 2
ctaccttggt at                                                              12

<210> SEQ ID NO 3
<211> LENGTH: 26
<212> TYPE: DNA
<213> ORGANISM: Artificial Sequence
<220> FEATURE:
<223> OTHER INFORMATION: tool for KIE measurement on DNMT1

<400> SEQUENCE: 3
actcatacca atcgatacca aggtag                                               26

<210> SEQ ID NO 4
<211> LENGTH: 26
<212> TYPE: DNA
<213> ORGANISM: Artificial Sequence
<220> FEATURE:
<223> OTHER INFORMATION: tool for KIE measurement on DNMT1
```

<400> SEQUENCE: 4
ctaccttggt atcgattggt atgagt                    26